United States Patent [19]

Soper, Jr.

[11] 4,021,306

[45] May 3, 1977

[54] PROCESS FOR THE PRODUCTION AND GERMINATION OF ENTOMOPHTHORA RESTING SPORES

[75] Inventor: Richard S. Soper, Jr., Orland, Maine

[73] Assignee: The United States of America as represented by the Secretary of Agriculture, Washington, D.C.

[22] Filed: Sept. 30, 1976

[21] Appl. No.: 728,105

Related U.S. Application Data

[62] Division of Ser. No. 681,962, April 30, 1976.

[52] U.S. Cl. .................................................. 195/81
[51] Int. Cl.² ........................................... C12B 1/00
[58] Field of Search .............................. 195/81, 72

[56] References Cited

UNITED STATES PATENTS 3,294,647  12/1966  Sehgal et al. ...................... 195/81

OTHER PUBLICATIONS

French, Journal of Agriculture Food Chemistry, vol. 19, No. 5, pp. 912–915 (1971).

Primary Examiner—Lionel M. Shapiro
Attorney, Agent, or Firm—M. Howard Silverstein; William E. Scott; David G. McConnell

[57] ABSTRACT

Production of Entomophthora resting spores was increased by 50 to 70% by modifying an egg yolk media with a particular maltose agar. Germination of the resting spores at levels up to 100% was obtained by preconditioning harvested spores by treatment with 95% ethanol, high speed blending, sonication, or a combination of ethanol treatment and high speed blending. Germination of spores which had been dried and stored but not pretreated as above was greatly increased by exposure to an atmosphere of 95% ethanol. In addition, treatment by the processes of this invention resulted in the production of a spore stage not previously observed or reported. Spores thus produced have been termed germ conidia.

9 Claims, No Drawings

PROCESS FOR THE PRODUCTION AND GERMINATION OF ENTOMOPHTHORA RESTING SPORES

This is a division of application Ser. No. 681,962, filed Apr. 30, 1976.

BACKGROUND OF THE INVENTION

1. Field of the Invention

This invention relates to the germination of resting spores and more particularly to methods for increasing significantly the number or percentage of resting spores that are germinated.

2. Description of the Prior Art

Entomophthora species are known to cause large scale epizootics and produce resting spores which might be stored for long periods. Consequently, these fungi are excellent candidates for biological control. However, the practical utilization of Entomophthora species as biological control agents has been hampered by the inability to produce large quantities of resting spores and induce their germination. Production of resting spores in artificial media and germination of the produced spores have been the problems.

In the past, many workers such as the following have attempted to germinate or increase the germination of resting spores; Nowakowski, Pamiet. Acad. Umiejejnosci zu Krakau 8, 153–183, 1884; Dustan, Proc. Acad. Entomol. Soc., 9, 14–36, 1924; Gilliatt, Proc. Acad. Entomol. Soc., 10, 46–54, 1925; Schweizer, Planta 35, 132–176, 1947; Hall and Halfhill, Jour. Econ. Entomol., 52, 30–35, 1959; and Krejzova, Jour. Invert. Pathol. 12, 460, 1968 and Ceska Mykol 25, 231–238, 1971. Although Hall and Halfhill reported one experiment in which 15% germination was obtained the level of germination obtained by the above workers was generally less than 5%. French and Gallimore (Agr. Food Chem 19, 912–915, 1971) reported on the effect of a number of chemical compounds on uredospore germination of wheat stem rust and found some of them to have a stimulatory effect. Ethanol, because it was found to be inactive and without any stimulatory effect on germination, was used to solubilize some of the nonwater-soluble, volatile, oily compounds. French and Weintraub (Arch. Biochem. and Biophys., 72, 235–237, 1957) has previously reported that extracts of uredospores of wheat stem rust contained substances capable of inducing germination of the dormant spores. They also found that the extracts contained at least two active compounds, one of which was pelargaraldehyde (n-nonanal) and showed that this compound stimulated germination of wheat rust spores to some extent. However, none of the prior art discloses any means of germinating resting spores that approaches the 100% level. Furthermore, none of the known procedures discloses a method or substance that is easily adaptable to large scale commercial size production and germination of resting spores.

SUMMARY OF THE INVENTION

It is therefore an object of this invention to provide a process for the production and germination of resting spores.

A further object of this invention is to provide a process for the production of large quantities of resting spores and for germination of these spores at levels up to 100%.

A still further object is to provide a process for producing and germinating resting spores in quantities adequate for use in the biological control of insects.

Another object is to provide a process for producing large quantities of Entomophthora resting spores and for germinating these spores at levels up to 100% for use in the biological control of aphids.

Still another object is to provide a process for germinating resting spores wherein the resting spores produce spores immediately after germination.

According to this invention the above objects are accomplished by producing the spores on a modified egg yolk media and then preconditioning them at harvest time. Standard egg yolk media was modified to make the media of this invention by adding molten Sabouraud maltose agar (SMA) to egg yolk and mixing immediately to prevent lumping of the agar. Harvested spores were then preconditioned according to this invention by contact with ethanol (95%), by high speed blending, by sonication, or by a combination of ethanol contact and high speed blending.

The processes of this invention resulted not only in increased production of resting spores and germination of the spores at levels up to 100%, but also in the production of a spore stage not previously observed. Quite unexpectedly, resting spores of *Entomophthora thaxteriana* were observed producing spores immediately after germination. This spore stage has not been previously observed or reported and, for the purposes of this invention, the spores thus produced have been termed germ conidia.

DETAILED DESCRIPTION OF THE INVENTION

Cultures of Entomophthora were obtained from diseased aphids collected from potato plants in northern Maine. The most frequently encounted pathogen was *E. nr. thaxteriana* from the green peach aphid, *Myzus persicae* (Sulzer) and the potato aphid, *Macrosiphum euphorbiae* (Thomas) (Environ. Ethomol 2, 346–347, and 3, 560–562, 1974). Initial isolation was made on egg yolk media as previously described (Entomophaga 4, 261–274, 1959) except that 30 ml. of molten Sabouraud maltose agar (SMA) were added to each 100 ml. of egg yolk. Sabouraud maltose agar is a readily available agar containing the following ingredients per liter: 10 gm. polypeptone (a pancreatic digest of casein and a peptic digest of animal tissue), 40 gm. maltose, and 15 gm. agar. Modification of the standard egg yolk media by addition of the molten SMA resulted, unexpectedly, in a great increase in production of resting spores. Insects were collected before eruption of the fungus through the cuticle. These were surface sterilized in streptomycin-penicillin (5,000 mcg-5,000 units/ml) and placed directly on the egg yolk media. The initial isolates were then transferred to slants of either Sabouraud dextrose agar (SDA) or SMA sealed with parafilm and stored at 20° C. to serve as stock cultures for future experiments. Following incubation at 25° C. for four to five weeks the medium had been entirely utilized and the majority of the fungus was in the resting spore state. The contents of 50 petri dishes were added to 2 liters of water and blended in a 5½ liter blendor. This was diluted again with 2 liters of distilled water, blended with a hand mixer, and centrifuged in a batch rotor in a refrigerated centrifuge once at 23,000 g for 20 minutes, twice at 10,000 g for 10 minutes, and once at 2,500 g for 10 minutes. Between each run the mycelium was easily discernible from the darker colored resting spores. The mycelium, being less dense than the spores, was at the surface and easily removed. Following initial clean up procedures the spores were re-suspended in distilled water and transferred to 50 ml centrifuge tubes. A similar procedure was followed as with the batch rotor except that mycelium was removed from the surface of the spores with a wash bottle. The purified resting spores were then spread upon 150 mm watch glass dishes and air dried. The drying chamber consisted of a plexiglass box 53 cm × 37 cm × 37 cm. Air was drawn through a descant (silica gel) and passed over the spores. After 18 to 20 hours the spores were removed from the dryer, placed in glass containers, and stored at 4° C. Standardized resting spore germination tests were used throughout the tests. Water agar (2%) was spread evenly over microscope slides and allowed to solidify. These were placed either in desiccators or supported on glass rods within large petri dishes (150 mm × 15 mm) with distilled water to maintain 100% relative humidity. Usually one ml of the streptomycin-penicillin concentration previously noted was added to each 100 ml of water agar to prevent bacterial contamination. Normal sterile precautions were used throughout.

The following method was used to determine germination. Resting spores samples to be tested were placed in suspension in sterile distilled water (1 mg/ml). The water agar slides were coated with the suspension (approx. 5 ml) and incubated at 25° C. for 48 hours. Germination began in 12 hours and usually was completed in about 72 hours. However, the proliferation of germ tubes and the disintegration of the empty germinated spores made determination of germination levels difficult after 48 hours. By this time, internal changes had taken place within the resting spores which were about to germinate. These spores are characterized by a densely granular endospore rather than a clear oil globule. At the end of the test period, the spores were stained with lactophenol aniline blue and a coverslip was added. Random microscope fields were selected until 100 spores had been counted. Each determination was replicated four times. A widefield microscope was used at 400 × magnification.

The production of spores by the process of this invention just described was from 50 to 70% greater than that obtained from egg yolk media without SAM. The spores obtained by this process were then used to develop procedures for increasing germination.

As previously stated, harvested spores were preconditioned by contact with ethanol (95%), by high speed blending, by sonication and by a combination of ethanol treatment and high speed blending. In addition, germination was greatly increased by exposing dried spores to an atmosphere of 95% ethanol just prior to being used.

Although many experimental avenues have been tried, the following procedure has been adopted for the production and germination of resting spores. The process was developed using Entomophthora spores; however, there is no reason that it should not be applicable to other resting spores.

Media Preparation

1. Surface sterilize hens' eggs in 2.5% sodium-hypoclorite for 30 minutes. If the egg white is to be saved, 50% ethanol may be substituted. It is important to use fresh, unwashed eggs. Eggs that have been washed prior to surface sterilization may be contaminated with bacteria.

2. Separate egg yolks aseptically into sterile tall widemouthed flasks (500 ml). A small teflon-coated stirring magnet is autoclaved within the flask to facilitate breaking the egg yolks.

3. Add 30 ml of molten SMA to each 100 ml of egg yolk. This must be mixed immediately upon addition to prevent lumping of the agar.

4. Pour media into 10 cm plastic petri dishes at the rate of approximately 25 ml per dish.

5. Coagulate the media in an isothermal autoclave at 80° C. for 7 minutes. Alternatively, coagulation can be accomplished in an oven at 80° C. for 20 minutes. If plastic petri dishes are utilized, it is important to note that only certain brands will withstand this temperature.

If the media is overcooked it becomes leathery and the fungi will not grow well. This is more likely to occur if dry heat is used for coagulation. If the media is not coagulated, resting spore formation will be very poor.

Inoculation of Media

6. Wrap the petri dishes containing the coagulated media in plastic film to prevent desiccation and store for 3 days to check for contamination.

7. Inoculate the plates by streaking with a sterile needle. The source of inoculum should be a vigorously growing culture between 4 and 7 days old.

8. Wrap the cultures in plastic film, incubate at 25° C. for 7 days, and unwrap. This allows the fungus to cover the entire medium and prevents excessive desiccation during the incubation period (4 to 5 weeks).

Extraction and Purification

9. Add the contents of 50 petri dishes to 2 liters of water.

10. At this point, one of the following five procedures is followed:
    a. Add ethanol (95%) to make the aqueous culture mixture approximately 1% ethanol and mix thoroughly (blend for about 5–10 minutes).
    b. Blend at high speed, approximately 10,000 to 14,000 rpm, for 30 minutes.
    c. Add ethanol (95%) to make the aqueous culture mixture approximately 1% ethanol and blend at high speed for 30 minutes.
    d. Sonicate for more than one minute.
    e. Mix thoroughly (blend for 5–10 minutes).

11. Store the blended cultures for 24 hours at 4° C. This step is used only if step 10(a) has been followed. When steps 10(b), 10(c) and 10(d) or 10(e) are followed, go directly to step 12.

12. Dilute with 2 liters of sterile distilled water, blend with a hand mixer, and centrifuge in a batch rotor. Centrifuge under refrigeration, once at 23,000 g for 20 minutes, twice at 10,000 g for 10 minutes, and once at 2,500 g for 10 minutes. The resting spores are packed tightly against the rotor wall, and the lighter mycelia are easily scraped from the surface.

13. Place in 50 ml tubes and centrifuge using angular head at 5,000 rpm for 10 minutes for final purification. The mycelia are easily washed from the surface of the spore pellet with a stream of distilled water from a plastic wash bottle.

14. Spread the pure spores on 150 mm watch glasses and place on racks within a plexiglass drying chamber.

Air is drawn by fan through silica gel and passed over the spores.

15. Remove the spores after 20 hours and place in sterile containers with a sachet of silica gel. Store at 4° C. until required.

From the foregoing treatments, the following germination was obtained: step 10(a), 30–40%; step 10(b), 35–55%; step 10(c), 50–100%; step 10(d), 30–50%. For the step 10(d) a 300 watt sonicator was used.

When spores from step 15, which has been prepared using step 10(e) were moistened and exposed to an atmosphers of 95% ethanol, 30–40% germination was obtained.

Step 11 was needed when the process followed step 10(a) so that the ethanol would be in contact with the culture for a longer period of time. The 5–10 minute blending in step 10(a) and 10(e) were needed to put the culture in suspension. However, this was proven not to have any effect on germination. Although storage at 4° C. provided the highest rates of germination, it is not a critical temperature. Any temperature below room temperature (20–23° C.) is sufficient.

In view of the fact that French and Gallimore, Supra, found ethanol to be inactive and not to have any stimulating effect on germination, it was very surprising and unexpected to obtain 30–40% germination from the preconditioning treatment with 95% ethanol. The stimulating effect of sonication was also completely unexpected bacause this procedure is routinely used to disintegrate cells. However, Entomophthora resting spores not only survived the treatment, but their rate of germination greatly increased. It was also found that sonication for at least one minute provided the desired effect and that sonication for longer periods of time did not further increase the amount of germination.

Although much of the work developing and verifying the utility of this invention was done with *Entomophthora thaxteriana*, other Entomophthora such as *E. aphids*, *E. blullata*, *E. exitialis*, *E. grylli*, *E. virulenta*, and an unnamed Entomophthora sp. from spruce budworm *Choristoneura fumiferana* (Clemens, when treated by the processes of this invention were found to yield increases in production of spores and rate of germination equal to those of *E. thaxteriana* and to produce germ conidia, the newly discovered spore stage.

I claim:

1. In a process for germinating resting spores wherein spores harvested from an inoculated media are put into an aqueous medium and then extracted, purified, dried and stored, the improvement comprising preconditioning the harvested spores prior to extracting and purifying them by adding to the spores in the aqueous medium 95% ethanol to make the aqueous medium approximately 1% ethanol and blending at approximately 10,000 to 14,000 rpm for 30 minutes.

2. The improvement of claim 1 wherein from 50 to 100% of the spores germinated.

3. The improvement of claim 2 wherein the resting spores produced germ conidia immediately after germinating.

4. In a process for germinating resting spores wherein spores harvested from an inoculated media are put into an aqueous medium and then extracted, purified, dried and stored, the improvement comprising preconditioning the harvested spores prior to extracting and purifying them by treating them according to a method selected from the groups consisting of (a) adding to the spores in the aqueous medium 95% ethanol to make the aqueous medium approximately 1% ethanol, mixing thoroughly, and storing for about 24 hours; (b) blending the spores in the aqueous medium at approximately 10,000 to 14,000 for 30 minutes; and (c) sonicating for more than one minute.

5. The improvement of claim 4 wherein from 30 to 55% of the spores germinated.

6. The improvement of claim 5 wherein the resting spores produced germ condia immediately after germinating.

7. In a process for germinating resting spores wherein harvested spores from an inoculated media are put into an aqueous medium and then extracted, purified, dried and stored, the improvement comprising moistening the dried spores and then exposing them to an atmosphere of 95% ethanol prior to germination.

8. The improvement of claim 3 wherein from 30 to 40% of the spores germinated.

9. The improvement of claim 8 wherein the resting spores produced germ condia immediately after germinating.

* * * * *